United States Patent [19]

Stanton et al.

[11] Patent Number: 4,599,357
[45] Date of Patent: Jul. 8, 1986

[54] 1-MERCAPTOALKANOYLINDOLINE-2-CARBOXYLIC ACIDS

[75] Inventors: James L. Stanton, Ossining; Norbert Gruenfeld, White Plains, both of N.Y.

[73] Assignee: Ciba-Geigy Corporation, Ardsley, N.Y.

[21] Appl. No.: 219,140

[22] Filed: Dec. 22, 1980

Related U.S. Application Data

[63] Continuation-in-part of Ser. No. 104,505, Dec. 17, 1979, abandoned.

[51] Int. Cl.$^4$ ............... A61K 31/40; C07D 209/26
[52] U.S. Cl. ................... 514/419; 514/414; 548/455; 548/491
[58] Field of Search ............ 260/326.11 R; 424/274; 548/455, 491; 514/414, 419

[56] References Cited

U.S. PATENT DOCUMENTS

| | | | |
|---|---|---|---|
| 3,184,466 | 5/1965 | Hennig et al. | 260/326.11 R |
| 3,780,062 | 12/1973 | Kaiser et al. | 260/326.11 R |
| 3,796,723 | 3/1974 | Kaiser et al. | 260/326.11 R |
| 4,046,889 | 9/1977 | Ondetti et al. | 260/239 A |
| 4,105,776 | 8/1978 | Ondetti et al. | 260/239 A |
| 4,256,750 | 3/1981 | Göring et al. | |
| 4,303,583 | 12/1981 | Kim et al. | |
| 4,396,773 | 8/1983 | Kim et al. | 548/491 |

FOREIGN PATENT DOCUMENTS

| | | |
|---|---|---|
| 0029488 | 9/1980 | European Pat. Off. |
| 0018104 | 10/1980 | European Pat. Off. |
| 0037231 | 7/1981 | European Pat. Off. |
| 0024852 | 11/1981 | European Pat. Off. |
| 3004370 | 8/1980 | Fed. Rep. of Germany |
| 2937779 | 4/1981 | Fed. Rep. of Germany |
| 5145664 | 11/1980 | Japan |
| 2027025 | 2/1980 | United Kingdom |

OTHER PUBLICATIONS

D. Cushman et al., Prog. Cardiovasc. Dis., XXI, No. 3 (Nov./Dec. 1978), pp. 176–182.
D. Cushman et al., Biochem., 16, No. 25 (1977), pp. 5484–5491.
U. Wolcke et al., Helv. Chim. Acta, vol. 53, Fasc. 7 (1970) Nr. 200, p. 1704.
Derwent Abstract of German Pat. No. DE 2,703,828.
H. C. J. Ottenheym et al., Approaches to Analogs of Anhydrogliotoxin, J. Am. Chem. Soc., 95, 1989 (1973), pp. 1991–1992.

*Primary Examiner*—Donald G. Daus
*Assistant Examiner*—Mary E. Ceperley
*Attorney, Agent, or Firm*—Norbert Gruenfeld; Harry Falber

[57] ABSTRACT

1-Mercaptoalkanoylindoline-2-carboxylic acids, e.g., those of the formula

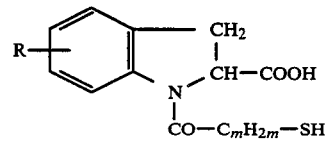

R = H, alkyl, alkoxy, halogeno or CF$_3$
m = 2–4 and functional derivatives thereof, are antihypertensive and cardioactive agents.

11 Claims, No Drawings

1-MERCAPTOALKANOYLINDOLINE-2-CARBOXYLIC ACIDS

CROSS-REFERENCE TO RELATED APPLICATION

This is a continuation-in-part of application Ser. No. 104,505, filed Dec. 17, 1979, now abandoned.

BACKGROUND OF THE INVENTION

1-Alkanoylindoline-2-carboxylic acids and their 5,6-dihydroxy-derivatives, i.e., N-acylated Cyclodopaderivatives, are described in Nippon Kagaku Zasshi 87, 760 (1966) and U.S. Pat. No. 3,796,723 or Helv. Chim. Acta 53, 1701 (1970) respectively, e.g., as synthetical examples of O- and/or N-acylations. Also, 1-mercaptoalkanoylpyrrolidine-2-carboxylic acids and their functional derivatives are known, e.g., Captopril according to U.S. Pat. No. 4,105,776, as possessing antihypertensive activity. Surprisingly it was found that either by introduction of a mercapto group into the former indolines, or by expansion of the latter pyrrolidines to the indoline ring-system, superior antihypertensive agents are obtained.

SUMMARY OF THE DISCLOSURE

The present invention concerns and has for its object the provision of new 1-mercaptoalkanoylindoline-2-carboxylic acids, more particularly of those corresponding to Formula I:

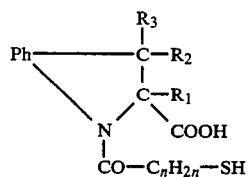

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; each of $R_1$, $R_2$ and $R_3$ is hydrogen or lower alkyl; and n is an integer from 1 to 7; the O- or S-lower alkanoyl or HPh-carbonyl derivatives of said phenols and/or mercaptans; the corresponding disulfide; the amide, lower alkyl esters or pharmaceutically acceptable salts of said acids; as well as of corresponding pharmaceutical compositions and of methods for the preparation and application of said products, which are useful antihypertensive and cardioactive agents.

DESCRIPTION OF THE PREFERRED EMBODIMENTS

The 1,2-phenylene group Ph and/or the phenyl group HPh, is preferably unsubstituted or monosubstituted, and its substituents are illustrated by the following groups; lower alkyl, e.g., methyl, ethyl, n- or i-propyl or -butyl; lower alkoxy, e.g., methoxy, ethoxy, n- or i-propoxy or -butoxy; lower alkylenedioxy, e.g., methylenedioxy, 1,1- or 1,2-ethylenedioxy; hydroxy; halogeno, e.g., fluoro, chloro or bromo; or trifluoromethyl.

Each of $R_1$, $R_2$ and $R_3$ is preferably hydrogen, but also lower alkyl, advantageously methyl, or another of those mentioned previously.

The term "lower", referred to above and hereinafter in connection with organic radicals or compounds respectively, defines such with up to 7, preferably up to 4, and advantageously but one or two carbon atoms.

The lower alkylene moiety $C_nH_{2n}$ is either straight, or preferably branched, and contains advantageously up to 4 carbon atoms. Thus, it represents above all ethylene, 1,2- or 1,3-propylene, but also methylene, 2-methyl-1,2- or -1,3-propylene, 1,2-, 1,3- or 1,4-butylene.

Said O- or S-lower alkanoyl or HPh-carbonyl derivatives, wherein either a phenolic HO-group within Ph, and/or the terminal HS-group is esterified, are preferably the acetyl, propionyl or pivaloyl; benzoyl, p-toluloyl, p-anisoyl or p-chlorobenzoyl derivatives; and said disulfide corresponds to two dehydro-moieties of Formula I, containing the disulfide ($S_2$) linking group.

The remaining functional derivatives are the carboxamide; lower alkyl, e.g., methyl, ethyl, n- or i-propyl or -butyl esters of said indoline-2-carboxylic acids; or preferably pharmaceutically acceptable metal or ammonium salts thereof, particularly alkali or alkaline earth metal salts, e.g., the sodium, potassium, magnesium or calcium salt; or advantageously easily crystallizing ammonium salts derived from ammonia or organic amines, such ass mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine dicyclohexylamine, triethanolamine, ethylenediamine, tris-hydroxymethyl)-aminomemethane or benzyl-trimethyl-ammonium hydroxide.

The compounds of this invention exhibit valuable pharmacological properties, primarily hypotensive, antihypertensive and cardioactive effects, inter alia due to their angiotensin converting enzyme inhibitory activity. This is demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs. Said compounds can be applied to them enterally or parenterally, advantageously orally or intravenously, for example within gelatin capsules or in the form of starchy suspensions or aqueous solutions respectively. The applied dosage may range between about 0.01 and 50 mg/kg/day, preferably between about 0.1 and 10 mg/kg/day, advantageously between about 1 and 5 mg/kg/day.

The in vivo lowering effect on the blood pressure is recorded either directly by means of a catheter, for example placed in the dog's femoral artery, or indirectly by sphygmamonometry at the rat's tail, and a transducer, expressing the blood pressure prior and after dosing in mm Hg. Thus, for example, the levorotatory 1-(3-mercapto-2S-methylpropanoyl)-indoline-2S-carboxylic acid, a representative member of the compounds of this invention, is very effective in said hypertensive rats and dogs at p.o.-doses as low or lower than 3 mg/kg/day. It also exhibits an inhibitory effect against the angiotensin I pressure response of normotensive rats.

They also exhibit an inhibitory effect against the angiotensin I pressure response of normotensive rats. The enzyme renin, normally causes specific hydrolysis of the circulating protein renin-substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100–120 mg/kg i.p. of sodium ethyl-(1-methylpropyl)-malonylthiourea. A femoral artery and saphenous vein are cannulated for direct blood pressure measurement and i.v. administration of angiotensin I and compounds of this invention. After the basal blood pressure is stabilized, pressor responses to 3 challenges of 0.33 µg/kg of angiotensin I i.v., in 5 minute intervals, are obtained. Such pressure responses are again obtained 5, 10, 15, 30 and 60 minutes after either i.v., or p.o. administration (stomach tube) of the compounds to be tested, and compared with the initial responses. Any observed decrease of said pressor response is an indication of angiotensin I converting enzyme inhibition, ranging up to 80% after 10 mg/kg i.v., or 50 mg/kg p.o. doses, which decrease may be sustained up to 60 minutes.

The in vitro inhibition of the angiotensin-converting enzyme by the compounds of this invention can be demonstrated analogous to Biochim. Biophys. Acta 293, 451 (1973). According to this method said compounds are dissolved at about 1 mM concentrations in phosphate buffer, externally cooled with ice. To these solutions various µl amounts of 1 mM of histidyl-leucine in phosphate buffer are added, followed by 100 µl of 5 mM hippuryl-histidyl-leucine in phosphate buffer and 50 µl of the angiotensin-converting enzyme, which is freshly prepared from lungs of adult male rabbits in Tris buffer, containing potassium and magnesium chloride, as well as sucrose. Said solutions are incubated at 37° for 30 minutes and combined with 0.75 ml of 0.6N aqueous sodium hydroxide to stop further reaction. Then 100 µl of o-phthalaldehyde are added at room temperature, and 10 minutes later 100 µl of 6N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the IC$_{50}$, i.e, the drug concentration which gives half the activity of the control sample containing no drug. Again, said representative member of the compounds of this invention is very effective in this in vitro test system, down to IC$_{50}$ values as low or lower than 2.6 nM.

Accordingly, the compounds of the invention are valuable antihypertensive agents, especially useful for ameliorating angiotensin-related (renal) hypertension and/or heart-conditions, such as congestive heart failure. They are also useful intermediates in the preparation of other valuable products, especially of corresponding pharmaceutical compositions.

Particularly useful for said purpose are those compounds of Formula I, wherein Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; each of $R_1$, $R_2$ and $R_3$ is hydrogen or lower alkyl; and n is an integer from 1 to 7; the O- or S-lower alkanoyl or HPh-carbonyl derivatives of said phenols and/or mercaptans; the corresponding disulfide; the amide, lower alkyl esters or pharmaceutically acceptable alkali metal, alkaline earth metal or ammonium salts of said acids.

More preferred are those compounds of Formula I, wherein Ph is 1,2-phenylene, unsubstituted or monosubstituted by lower alkyl, lower alkoxy, lower alkylenedioxy, hydroxy, halogeno or trifluoromethyl; each of $R_1$, $R_2$ and $R_3$ is hydrogen or methyl; and n is an integer from 1 to 7; and said functional O-, S- and/or acid derivatives listed in the previous paragraph.

Expecially valuable compounds of this invention are those of Formula II

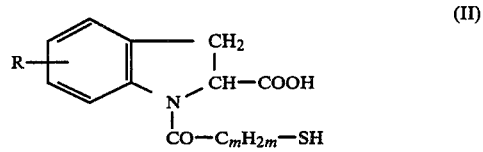

(II)

wherein R is hydrogen, alkyl or alkoxy with up to 4 carbon atoms, halogeno or trifluoromethyl and m is an integer from 2 to 4; the S-lower alkanoyl or benzoyl derivatives thereof; the corresponding disulfide; lower alkyl esters or pharmaceutically acceptable alkali metal or ammonium salts of said acids.

An embodiment of the invention comprises compounds of the formula

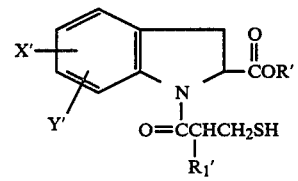

wherein
$R_1'$ is H or CH$_3$,
R' is H or lower alkyl,
X' is H, methoxy, hydroxy, Cl or CH$_3$,
Y' is H or methoxy,
or X' and Y' are on adjacent carbon atoms and together form a methylenedioxy group.

The most preferred compounds of this invention are those of Formula II, wherein R is hydrogen, methyl, methoxy, fluoro, chloro or trifluoromethyl, advantageously in the 5-position, and $C_m H_{2m}$ is ethylene or 1,2-propylene; and said S- and/or acid derivatives listed in the preceding paragraph, advantageously the levorotatory optical antipodes thereof with 2S-carboxy and 2S-methyl within said indoline and 1,2-propylene moieties respectively.

The compounds of this invention are prepared according to conventional methods, i.e., analogous those of DE No. 2,703,828, advantageously by:

(1) condensing compounds of Formulae III and IV

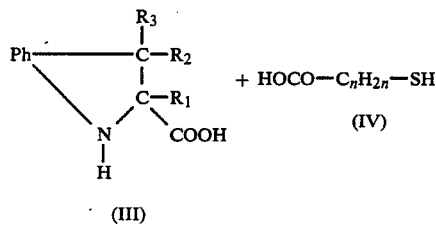

or said O-, S- or acid derivatives thereof, or reactive functional derivatives of said compounds IV, or (2), reacting compounds of Formulae V and VI

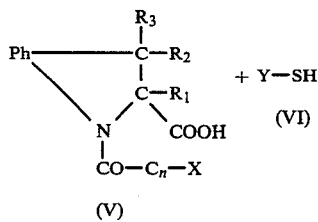

or said O-, S- or acid derivatives thereof, wherein X is either $H_{2n-1}$, or reactively modified $H_{2n}$—OH, and Y is hydrogen, an alkali metal or said acyl radicals.

Reactive functional derivatives of compounds IV are preferably acid halides, esters, simple or mixed anhydrides, such as the chloride, lower alkyl esters, the thiolactone, acetic or cyanoacetic anhydride, or the corresponding Woodward-reagent. Said condensation occurs either spontaneously, or in the presence of condensing agents, such as dicyclohexylcarbodiimide.

A reactively modified $H_{2n}$—OH group is advantageously esterified with a strong inorganic or organic acid, such as a hydrohalic, e.g., hydrochloric or hydrobromic acid; or an aliphatic or aromatic sulfonic acid, e.g., methane, p-toluene or m-bromobenzene sulfonic acid. Said reaction with the unsaturated compounds (X is $H_{2n-1}$) is preferably performed with thioacids (Y is alkanoyl or HPhCO), whereas said reactive esters (e.g., X is $H_{2n}$—Br) are preferably reacted with the corresponding salts of Y—SH, e.g., sodium hydrosulfide, disulfide, thioacetate or thiobenzoate.

The compounds of Formula I, or said O-, S- or acid derivatives thereof, so obtained, can be converted into each other according to conventional methods. Thus, for example, resulting phenols and/or mercaptans may be acylated with corresponding lower alkanoyl or aroyl halides, esters or anhydrides; or resulting acyl derivatives hydrolyzed, ammonolyzed or hydrazinolyzed. Free mercaptans may be oxidized to the corresponding disulfides, e.g., by air-oxidation, or with the use of mild oxidation agents, such as iodine in alkanolic solution. Conversely, resulting disulfides may be reduced to the corresponding mercaptans, for example with catalytically activated or nascent hydrogen, such as hydrogen generated from metals and acids, e.g., zinc and acetic acid, or with mild reducing agents, such as complex light metal hydrides, e.g., sodium borohydride. In the course of said ammonolyzing de-acylation, esters may be converted into amides, or the latter generated with ammonia directly; or resulting esters may be hydrolyzed, for example with aqueous alkalies, such as alkali metal carbonates or hydroxides. Resulting free acids may be esterified with either lower alkanols, or diazoalkanes, or converted into said metal or ammonium salts in conventional manner.

The starting material of Formulae III to VI is known, or, if new, may be prepared according to conventional methods, e.g., those illustrated by the examples herein.

In case mixtures of geometrical or optical isomers of the above compounds of Formulae I to VI are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d- or l-(tartrates, mandelates, camphorsulfonates, or 1-naphthyl-1-ethylisocyanates), or of d- or l-(α-methylbenzylammonium, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g., those of Formula II.

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcllulose, sodium carboxymethylcellulose and/or polyvinylpyrrolidone, if desired, (d) disintegrants, e.g., starches, agar, alginic acid or its sodium salt, enzymes of the binders or effervescent mixtures and/or (e) absorbents, colorants, flavors and sweeteners. Injectable compositions are preferably aqueous isotonic solution or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively, and contain about 0.1 to 75%, preferably about 1 to 50% of the active ingredient. A unit dosage for a mammal of about 50–70 kg weight may contain between about 10 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To the stirred mixture of 5.0 g of indoline-2-carboxylic acid methyl ester [J. Am. Chem. Soc. 92, 2476 (1970)], 7.8 g of powdered potassium carbonate and 50 ml of methylene chloride, 5.1 g of 3-acetylthio-2-methylpropanoyl chloride (Belgium Pat. No. 868,532) in 20 ml of methylene chloride are added during 3 minutes at room temperature. After 2 hours the mixture is diluted with 100 ml of methylene chloride and washed with 100 ml of water, 100 ml of 1N hydrochloric acid and 100 ml of saturated aqueous sodium bicarbonate. The organic layer is dried and evaporated, to give the 1-(3-acetylthio-2-methylpropanoyl)-indoline-2-carboxylic acid methyl ester as an oil, showing in the IR-spectrum bands at 1710, 1690 and 1675 cm$^{-1}$.

EXAMPLE 2

The solutions of 4.5 g of 1-(3-acetylthio-2-methylpropanoyl)-indoline-2-carboxylic acid methyl ester in 25 ml of methanol, and 19.9 ml of 2.08N aqueous potassium hydroxide are each deoxygenated by bubbling nitrogen through them for 10 minutes. Then the latter solution is added to the former and the mixture is stirred at room temperature under nitrogen. After 2 hours 30 ml of 3N hydrochloric acid and 100 ml of water are added and the mixture is extracted twice with 150 ml of diethyl ether. The extract is dried, evaporated and 3.3 g of the residue combined with 2.3 g of dicyclohexylamine in 100 ml of methylene chloride. The solvent is evaporated and the salt recrystallized from acetonitrile to give the dicyclohexylammonium 1-(3-mercapto-2-methylpropanoyl)-indoline-2-carboxylate melting at 181°–186°.

EXAMPLE 3

To the mixture of 7.8 g of powdered potassium carbonate, 5.0 g of indoline-2-carboxylic acid methyl ester and 50 ml of methylene chloride, 4.7 g of 3-acetylthiopropanoyl chloride [Helv. Chim. Acta 40, 2148 (1957)] in 10 ml of methylene chloride are added at room temperature. After 1 hour the mixture is diluted with 100 ml of methylene chloride and washed with 50 ml of water, 50 ml of 1N hydrochloric acid and 50 ml of saturated aqueous sodium bicarbonate. The organic layer is dried and evaporated, to give the 1-(3-acetylthiopropanoyl)-indoline-2-carboxylic acid methyl ester as an oil, showing IR-bands at 1710, 1690 and 1640 cm$^{-1}$.

EXAMPLE 4

The solutions of 4.0 g of 1-(3-acetylthiopropanoyl)-indoline-2-carboxylic acid methyl ester in 20 ml of methanol and 18.5 ml of 2.11N aqueous potassium hydroxide are each deoxygenated by bubbling nitrogen through them for 10 minutes. Then the latter solution is added to the former and the mixture stirred at room temperature under nitrogen. After 2 hours it is quenched with 50 ml of 1N hydrochloric acid and extracted twice with 100 ml of diethyl ether. The combined extracts are dried and evaporated, to give the 1-(3-mercaptopropanoyl)-indoline-2-carboxylic acid melting at 140°–142°.

EXAMPLE 5

To the solution of 23.6 g of indoline-2S-carboxylic acid ethyl ester in 250 ml of methylene chloride, 34 g of powdered potassium carbonate are added while stirring at room temperature, followed by 22.3 g of 3-acetylthio-2S-methylpropanoyl chloride in 50 ml of methylene chloride during 30 minutes. The mixture is stirred for 2 hours at room temperature and then partitioned between 500 ml of diethyl ether and 100 ml of water. The organic layer is washed with 100 ml of water, twice with 100 ml of 1N hydrochloric acid and once with 50 ml of saturated aqueous sodium chloride, dried and evaporated, to yield the 1-(3-acetylthio-2S-methylpropanoyl)-indoline-2S-carboxylic acid ethyl ester; $[\alpha]_D = -198.6°$ (c=1.3 in ethanol).

The starting material is prepared as follows:

120 g of 1-acetylindoline-2-carboxylic acid [Nippon Kagaker Zasshi 87, 760 (1966)] and 172 g of l-cinchonidine are dissolved in 1,200 ml of hot ethanol. The solution is allowed to stand at room temperature overnight and then at 0° for 4 days. The white crystalline salt is filtered off and discarded. The filtrate is evaporated, 1,000 ml of water are added and the solution is adjusted to pH=1 with concentrated hydrochloric acid. After 15 minutes the product is collected by filtration and washed thrice with 250 ml of 2N aqueous hydrochloric acid, twice with 500 ml of water and twice with 100 ml of ethanol, to give the 1-acetylindoline-2S-carboxylic acid melting at 214°–215°; [α]$_D$=−133.3° (c=1.165 in ethanol).

The suspension of 37.5 g thereof in 380 ml of 2N aqueous hydrochloric acid is deoxygenated by bubbling nitrogen through it for 5 minutes, followed by refluxing for 2 hours. It is cooled to room temperature, filtered through infusorial earth, the filtrate evaporated and the residue crystallized from diethyl ether-isopropanol, to yield the indoline-2S-carboxylic acid hydrochloride melting at 133° (dec.); [α]$_D$=−70.4 (c=1 in ethanol).

The solution of 34 g thereof in 350 ml of ethanol is saturated with dry hydrogen chloride without external cooling. The mixture is stirred for 2 hours at room temperature and the solvent removed until crystallization begins. The concentrate is poured into 400 ml of diethyl ether, cooled at 0° for 1 hour and filtered, to yield the indoline-2S-carboxylic acid ethyl ester hydrochloride melting at 179°–181°; [α]$_D$=−63° (c=1.385 in ethanol).

29.8 g thereof are partitioned between 300 ml of saturated aqueous sodium bicarbonate and 100 ml of methylene chloride. The aqueous layer is extracted twice with additional 100 ml of methylene chloride, the combined organic layers washed with saturated aqueous sodium chloride and evaporated, to yield the indoline-2S-carboxylic acid ethyl ester as an oil, showing the major IR-band at 1730 cm$^{-1}$.

EXAMPLE 6

The solutions of 40.2 g of 1-(3acetylthio-2S-methylpropanoyl)-indoline-2S-carboxylic acid ethyl ester in 200 ml of methanol, and 183 ml of 2.06N aqueous potassium hydroxide are each deoxygenated by bubbling nitrogen through them for 10 minutes. The latter solution is then added to the former and the mixture stirred at room temperature under nitrogen for 2 hours. It is diluted with 100 ml of water and washed with 100 ml of diethyl ether. The aqueous layer is made acidic by addition of 150 ml of 4N aqueous hydrochloric acid and the mixture extracted thrice with 100 ml of methylene chloride. The combined extracts are washed with saturated aqueous sodium chloride, dried and evaporated. The residue is dissolved in 100 ml of diethyl ether and 100 ml of hexane are added. The solution is left standing at 0° overnight, producing a white precipitate, which is collected by filtration, to yield the 1-(3-mercapto-2S-methylpropanoyl)-indoline-2S-carboxylic acid melting at 141°–142°; [α]$_D$=−178.2° (c=1.785 in ethanol).

EXAMPLE 7

To the stirred mixture of 4.0 g of 5-methoxyindoline-2-carboxylic acid ethyl ester, 5.0 g of powdered potassium carbonate and 50 ml of methylene chloride, 3.3 g of 3-acetylthio-2-methylpropanoyl chloride in 10 ml of methylene chloride are added during 1 minute. After stirring for 2 hours at reflux the mixture is cooled to room temperature and partitioned between 50 ml of water and 100 ml of diethyl ether. The organic layer is washed with 50 ml of water, 50 ml of 1N hydrochloric acid and 50 ml of saturated aqueous sodium chloride, dried and evaporated, to give the 1-(3-acetylthio-2-methylpropanoyl)-5-methoxyindoline-2-carboxylic acid ethyl ester as an oil.

The solutions of 6.6 g thereof in 30 ml of methanol, and 29 ml of 1.93N aqueous potassium hydroxide are each deoxygenated by bubbling nitrogen through them for 10 minutes. Then the latter solution is added to the former and the mixture is stirred at room temperature under nitrogen. After 2 hours the mixture is quenched with 30 ml of 4N hydrochloric acid and diluted with 50 ml of water. It is extracted twice with 100 ml of diethyl ether, the extract dried and evaporated. 4.1 g of the residue are dissolved in 70 ml of diethyl ether and 2.8 ml of dicyclohexylamine are added, producing the white crystalline dicyclohexylammonium 1-(3-mercapto-2-methylpropanoyl)-5-methoxyindoline-2-carboxylate melting at 199°–202°.

The starting material is prepared as follows: The mixture of 20 g of 5-methoxyindole-2-carboxylic acid (J. Chem. Soc. 1970, 865) and 200 ml of acetic anhydride is refluxed for 2 hours and allowed to cool to room temperature. It is filtered, the filtrate evaporated and the residue is stirred in 300 ml of water. Excess sodium bicarbonate is added, the mixture stirred for 3 hours and then washed with 200 ml of diethyl ether. The aqueous layer is acidified to pH=1 with concentrated hydrochloric acid and filtration yields the 1-acetyl-5-methoxyindole-2-carboxylic acid melting at 173°–175°.

The solution of 16.5 g thereof in 250 ml of ethanol is hydrogenated at one atmosphere in the presence of 1.0 g of platinum oxide. After 2 hours the mixture is filtered and the filtrate concentrated to 100 ml. After standing at 0° overnight it is filtered, to give the white crystalline 1-acetyl-5-methoxindoline-2-carboxylic acid melting at 164°–167°.

6.0 g thereof are refluxed in 60 ml of 2N aqueous hydrochloric acid for 2 hours and the mixture is evaporated. The residue is dissolved in 50 ml of isopropanol and diethyl ether is added until the solution becomes turbid. After cooling at 0° the precipitate is filtered off, to yield the 5-methoxyindoline-2-carboxylic acid hydrochloride melting at 90°–92° (dec.).

The solution of 5.5 g thereof in 50 ml of ethanol is saturated with gaseous hydrogen chloride without external cooling and stirred at room temperature for 1 hour. The mixture is evaporated, the residue dissolved in 50 ml of water and the solution is washed with diethyl ether. The aqueous layer is adjusted to pH=10 with aqueous ammonium hydroxide, extracted twice with 50 ml of methylene chloride, the combined extracts are dried and evaporated, to give the 5-methoxyindoline-2-carboxylic acid ethyl ester as an oil.

EXAMPLE 8

The solution of 3.6 g of 3-acetylthiopropanoyl chloride in 10 ml of methylene chloride is added dropwise while stirring under nitrogen to the suspension of 5.4 g of 5,6-dimethoxyindoline-2-carboxylic acid ethyl ester and 5.96 g of powdered potassium carbonate in 40 ml of methylene chloride. The mixture is stirred for 2 hours at room temperature, filtered and the filtrate washed successively with saturated aqueous sodium bicarbonate, water, 0.5N hydrochloric acid and water. The organic solution is dried, evaporated, the residue crystallized from petroleum ether and further purified by slurrying in diethyl ether for 2 hours, to yield the 1-(3-acetylthiopropanoyl)-5,6-dimethoxyindoline-2-carboxylic acid ethyl ester melting at 104°–106°.

To the suspension of 5.0 g thereof in 60 ml of methanol the solution of 1.57 g of sodium hydroxide in 20 ml of water is added while stirring at room temperature under nitrogen for 1.5 hours. The methanol is removed by distillation, the aqueous solution washed with methylene chloride and diethyl ether and acidified with 6N hydrochloric acid. The resulting precipitate is filtered off and discarded. The aqueous filtrate is extracted with methylene chloride, the extract dried, evaporated and the residue crystallized from diethyl ether, to give the 1-(3-mercaptopropanoyl)-5,6-dimethoxyindoline-2-carboxylic acid melting at 182°–184°.

The corresponding disulfide, i.e., the 1,1'-[dithiobis-(3-propanoyl)]-bis-5,6-dimethoxyindoline-2-carboxylic acid, m.p. 217°–219°, is obtained when the aqueous solution of the sodium 1-(3-mercaptoprapanoyl)-5,6-dimethoxyindoline-2-carboxylate is allowed to stand at room temperature overnight in the open air, and the free acid is regenerated as shown above.

The starting material is prepared as follows: The suspension of 10.8 g of 5,6-dimethoxyindole-2-carboxylic acid in 150 ml of acetic anhydride is heated at the steam bath for 15 minutes and the mixture evaporated at 65°–70°. The residue is added to the mixture of 30 g of sodium bicarbonate and 200 ml of water and the mixture heated at the steam bath for 20 minutes. It is filtered, cooled and acidified with concentrated hydrochloric acid, filtered again and the residue suspended in 300 ml of methanol. The suspension is hydrogenated overnight in the presence of 1 g of platinum oxide at room temperature and atmospheric pressure. Removal of the catalyst and evaporation of the solvent yields the crude 1-acetyl-5,6-dimethoxyindoline-2-carboxylic acid. Hydrolysis in 90 ml of 2N hydrochloric acid under reflux overnight, washing with diethyl ether and evaporation of the aqueous solution yields the hygroscopic 5,6-dimethoxyindoline-2-carboxylic acid hydrochloride. It is esterified with ethanolic hydrogen chloride at room temperature for 3 hours to give the 5,6-dimethoxyindoline-2-carboxylic acid ethyl ester showing IR-bands at 3500 and 1740 cm$^{-1}$.

EXAMPLE 9

To the solution of 0.35 g of sodium in 50 ml of ethanol, 1.2 g of thioacetic acid are added and the mixture stirred for 0.5 hours at room temperature. Then 4.5 g 1-(2-bromopropanoyl)-indoline-2-carboxylic acid ethyl ester are added and the mixture is refluxed for 8 hours. It is cooled to room temperature, evaporated, and the residue partitioned between 30 ml of methylene chloride, 70 ml of diethyl ether and 50 ml of water. The organic layer is dried and evaporated, to yield the 1-(2-acetylthiopropanoyl)-indoline-2-carboxylic acid ethyl ester as an oil.

The solutions of 4.5 g thereof in 50 ml of methanol, and 22 ml of 2.03N aqueous potassium hydroxide are each deoxygenated by bubbling nitrogen through them. Then the latter solution is added to the former and the mixture stirred at room temperature under nitrogen. After 2 hours it is quenched with 75 ml of 1N hydrochloric acid and extracted twice and 100 ml of methylene chloride. The combined extracts are dried, evaporated, the residue dissolved in 100 ml of diethyl ether and 2.5 g of dicyclohexylamine are added, producing the dicyclohexylammonium 1-(2-mercaptopropanoyl)-indoline-2-carboxylate melting at 205°–206°.

The starting material is prepared as follows: To 2.7 g of indoline-2-carboxylic acid ethyl ester and 3.4 g of powdered potassium carbonate in 30 ml of methylene chloride, 2.42 g of 2-bromopropanoyl chloride in 10 ml of methylene chloride are added during 2 minutes. The mixture is stirred at room temperature for 2 hours and then partitioned between 50 ml of water and 100 ml of diethyl ether. The organic layer is washed twice with 30 ml of 1N hydrochloric acid and 25 ml of saturated aqueous sodium chloride, dried and evaporated, to yield the 1-(2-bromopropanoyl)-indoline-2-carboxylic acid ethyl ester melting at 101°–103°.

EXAMPLE 10

To the mixture of 1.4 g of indoline-2-carboxylic acid methyl ester, 2.2 g of powdered potassium carbonate and 25 ml of methylene chloride, 1.54 g of 3-acetylthiopivaolyl chloride in 5 ml of methylene chloride are added during 2 minutes. The mixture is refluxed for 3 hours and then cooled to room temperature. It is diluted with 100 ml of methylene chloride and washed with 50 ml of water, 50 ml of 1N hydrochloric acid and 25 ml of saturated aqueous sodium chloride, dried and evaporated, to yield the oily 1-(3-acetylthio-2,2-dimethylpropanoyl)-indoline-2-carboxylic acid methyl ester.

The solutions of 2.7 g thereof in 20 ml of methanol, and 25.4 ml of 2.08N aqueous potassium hydroxide are each deoxygenated by bubbling nitrogen through them for 10 minutes. Then the latter solution is added to the former and the mixture is stirred at room temperature under nitrogen for 4 hours. It is quenched with 15 ml of 4N hydrochloric acid, followed by 50 ml of water, and extracted twice with 100 ml of methylene chloride. The combined extracts are dried, evaporated and the residue crystallized from diethyl ether, to give the 1-(3-mercaptopivaloyl)-indoline-2-carboxylic acid melting at 136°–138°.

The starting material is prepared as follows: The mixture of 50 g of 3-chloropivalic acid, 4.2 g of potassium thioacetate, 1 g of potassium iodide and 200 ml of ethanol is refluxed for 18 hours. It is cooled to room temperature, filtered, the filtrate evaporated and the residue partitioned between 100 ml of water and 200 ml of diethyl ether. The aqueous layer is extracted with 100 ml of diethyl ether, the combined organic layers dried, evaporated and the residue distilled at 150°–155°/3 mm Hg, to yield the 3-acetylthiopivalic acid.

28.3 g thereof are stirred in 35 ml of thionyl chloride at 60° for 2.5 hours. The excess thionyl chloride is evaporated and the residue distilled at 85°–92°/3 mmHg, to give the 3-acetylthiopivaloyl chloride showing IR-bands at 1780, 17445 and 1700 cm$^{-1}$.

EXAMPLE 11

0.93 g of triethylamine are added to the suspension of 0.7 g of 3,3-dimethylindoline-2-carboxylic acid hydrochloride in 20 ml of methylene chloride and the resulting solution is cooled to −10°. The solution of 0.51 g of 3-acetylthiopropanoyl chloride in 5 ml of methylene chloride is added dropwise and the mixture stirred at −5° to −10° for 1 hour and at room temperature for 3 hours. It is cooled to 0° and treated with 10 ml of 3N hydrochloric acid. The organic layer is separated and the aqueous solution further extracted with methylene chloride. The combined methylene chloride solutions are dried and evaporated, to give the 1-(3-acetylthiopropanoyl)-3,3-dimethylindoline-2-carboxylic acid as a foam.

The solution of 0.9 g thereof in 8.4 ml of methanol and 8.4 ml of 1N sodium hydroxide is stirred at room temperature under nitrogen for 40 minutes. It is cooled, acidified with 6N hydrochloric acid and extracted 3 times with diethyl ether. The extract is dried, evaporated and the residue crystallized from hexane, to yield the 1-(3-mercaptopropanoyl)-3,3-dimethylindoline-2-carbolic acid melting at 94°–96°

The starting material is prepared as follows: The solution of 8.0 g of 3,3-dimethylindolenine-2-carboxylic acid ethyl ester [J. Am. Chem. Soc., 95, 1989 (1974)] in 100 ml of ethanol is hydrogenated overnight in the presence of 0.8 g of 5% rhodium on carbon at room temperature and 3 atmospheres. The mixture is filtered, evaporated and the residual oil treated with ethanolic hydrochloric acid. The resulting product is filtered off and slurried in ethyl acetate, to give the ethyl 3,3-dimethylindoline-2-carboxylate hydrochloride melting at 156°–158°.

The solution of 1 g thereof in 10 ml of 3N hydrochloric acid is heated under reflux for 3 hours and evaporated to dryness to give the 3,3-dimethylindoline-2-carboxylic acid hydrochloride melting at 209°–211°.

EXAMPLE 12

To the suspension of 1.0 g of 1-(3-mercaptopropanoyl)-indoline-2-carboxylic acid in 20 ml of water is added 1N aqueous sodium hydroxide to reach the pH=6.5 at 0°. Thereupon the solution of 0.5 g of iodine in 10 ml of ethanol is added dropwise during 5 minutes and the pH of the mixture is readjusted to 6.5 by addition of 1N aqueous sodium hydroxide. The mixture is stirred for 15 minutes and then quenched with 10 ml of 1N hydrochloric acid, producing a precipitate which is filtered off, to yield the 1,1'-[dithiobis-(3-propanoyl)]-bis-indoline-2-carboxylic acid melting at 170°–172°.

Analogously the 1,1'-[dithiobis-3-(2S-methylpropanoyl)]-bis-indoline-2S-carboxylic acid is prepared from the compound of Example 6, melting at 135°–138°; $[\alpha]_D = -16.1°$ (c=1.32 in ethanol).

EXAMPLE 13

The mixture of 0.2 g of 1,1'-[dithiobis-(3-propanoyl)]-bis-5,6-dimethoxyindoline-2-carboxylic acid, 20 ml of 1N sulfuric acid, 20 ml of methanol and 0.1 g of tin is stirred at room temperature overnight under nitrogen. The mixture is worked up as shown in Example 8, to yield the 1-(3-mercaptopropanoyl)-5,6-dimethoxyindoline-2-carboxylic acid, which is identical with that obtained according to said example, e.g., by comparing their thin layer chromatogram on silica gel with chloroform-ethanol-acetic acid (80:10:1) as moving phase.

EXAMPLE 14

The mixture of 3.0 g of 1-methacryloylindoline-2-carboxylic acid ethyl ester and 0.97 g of thioacetic acid is stirred under nitrogen at room temperature for 4 days. Traces of thioacetic acid are removed by distillation, to give the 1-(3-acetylthio-2-methylpropanoyl)-indoline-2-carboxylic acid ethyl ester, showing peaks in the NMR-spectrum at 9.45, 2.33 and 1.25 ppm. Said compound can also be prepared analogous to the method illustrated by Example 1.

The starting material is prepared as follows: To the mixture of 3.0 g of indoline-2-carboxylic acid ethyl ester, 4.3 g of powdered potassium carbonate and 30 ml of methylene chloride is added 1.64 g of methacryloyl chloride in 5 ml of methylene chloride during 1 minute. After stirring at room temperature for 3 hours the mixture is partitioned between 50 ml of water and 100 ml of diethyl ether. The organic layer is washed with 30 ml of 1N hydrochloric acid and 25 ml of saturated sodium chloride, dried and evaporated, to yield the 1-methacryloylindoline-2-carboxylic acid ethyl ester as an oil.

EXAMPLE 15

To the mixture of 5.0 g of indoline-2-carboxylic acid hydrochloride and 50 ml of methylene chloride are added 7.9 g of triethylamine, and after 5 minutes 6.1 g of 3-benzoylthio-2-methylpropanoyl chloride during 3 minutes. After stirring the mixture at room temperature for 2 hours, it is extracted thrice with 50 ml of saturated aqueous sodium bicarbonate. The combined aqueous solutions are adjusted to pH=1 with 4N hydrochloric acid and reextracted thrice with 50 ml of methylene chloride. The combined extracts are dried and evaporated, to yield the 1-(3-benzoylthio-2-methylpropanoyl)-indoline-2-carboxylic acid.

The solution of 9.2 g thereof in 100 ml of methanol is saturated with gaseous ammonia and the mixture evaporated. The residue is partitioned between 75 ml of water and 50 ml of methylene chloride, the aqueous layer washed with 50 ml of methylene chloride and then adjusted to pH=1 with concentrated hydrochloric acid. The aqueous layer is extracted twice with 50 ml of methylene chloride, the combined extracts dried, evaporated, and the residue converted into the dicyclohexylammonium salt, to yield the product of Example 2; m.p. 181°–186°.

EXAMPLE 16

To the mixture of 0.50 g of indoline-2-carboxylic acid ethyl ester, 0.72 g of powdered potassium carbonate and 20 ml of methylene chloride is added 0.32 g of 3,3'-dithiodipropanoyl chloride in 5 ml of methylene chloride during 1 minute. After stirring at room temperature for 2 hours the mixture is diluted with 100 ml of methylene chloride and washed with 50 ml of water, 50 ml of 1N hydrochloric acid and 50 ml of saturated aqueous sodium bicarbonate. The organic layer is dried and evaporated to yield the 1,1'-[dithiobis-(3-propanoyl)]-bis-indoline-2-carboxylic acid ethyl ester, showing IR-bands at 1715 and 1655 cm$^{-1}$.

EXAMPLE 17

To the solution of 0.45 g of 1,1'-[dithiobis-(3-propanoyl)]-bis-indoline-2-carboxylic acid ethyl ester, in 10 ml of methanol is added 0.92 ml of 2.03N aqueous potassium hydroxide followed by 5 ml of water at room temperature. The mixture is stirred for 3 hours and then quenched with 10 ml of 1N hydrochloric acid. After stirring for 10 minutes a white crystalline product appears, which is collected by filtration to give the 1,1'-[dithiobis-(3-propanoyl)]-bis-indoline-2-carboxylic acid, melting at 170°–172°. It is identical with that prepared according to Example 12.

EXAMPLE 18

To the mixture of 2.3 g of indoline-2S-carboxylic acid ethyl ester, 3.3 g of powdered potassium carbonate and 50 ml of methylene chloride is added 2.9 g of 3-benzoylthio-2S-methylpropanoyl chloride during 1 minute. After stirring 2 hours at room temperature the mixture is diluted with 100 ml of methylene chloride and washed with 50 ml of water, 50 ml of 1N hydrochloric acid and 50 ml of saturated aqueous sodium bicarbonate. The organic layer is dried, evaporated and the residue slurried in 25 ml of hexane to give the 1-(3-benzoylthio-2S-methylpropanoyl)-indoline-2S-carboxylic acid ethyl ester, melting at 114°–116°; $[\alpha]_D = -195.9$ (C=1.5 in ethanol).

EXAMPLE 19

The solution of 1.5 g of 1-(3-benzoylthio-2S-methylpropanoyl)-indoline-2S-carboxylic acid ethyl ester in 50 ml of methanol is saturated with gaseous ammonia and stirred at room temperature for 2 hours. Thereupon, 3.7 ml of 2N aqueous potassium hydroxide are added, followed by 50 ml of water, and the mixture is stirred for 1.5 hours. The methanol is evaporated, 50 ml of water are added and the mixture is filtered. The filtrate is washed twice with 50 ml of ethyl acetate, acidified with 25 ml of 1N hydrochloric acid and extracted twice with 50 ml of methylene chloride. The extract is dried, evaporated and the residue crystallized from hexane-diethyl ether, to give the 1-(3-mercapto-2S-methylpropanoyl)-indoline-2S-carboxylic acid, melting at 140°–142°; $[\alpha]_D = -177°$ (c=1.1 in ethanol); it is identical with that of Example 6.

EXAMPLE 20

To the solution of 2.0 g of 1-(3-benzoylthio-2S-methylpropanoyl)-indoline-2-carboxylic acid ethyl ester in 30 ml of methylene chloride is added 0.3 g of hydrazine hydrate while stirring at room temperature. After 3 days the mixture is washed thrice with 30 ml of 1N hydrochloric acid, dried and evaporated, to yield the 1-(3-mercapto-2S-methylpropanoyl)-indoline-2-carboxylic acid ethyl ester, showing IR bands at 1715 and 1660 cm$^{-1}$.

EXAMPLE 21

The solution of 0.052 g of 3-acetylthiopropanoyl chloride in 1 ml of methylene chloride is added slowly to the mixture of 60 mg of 3,3-dimethylindoline-2-carboxamide, 87 mg of potassium carbonate and 9 ml of methylene chloride. The mixture is stirred at room temperature overnight, diluted with methylene chloride and filtered. The filtrate is washed with saturated aqueous sodium bicarbonate, water, 0.5N hydrochloric acid and water, dried, evaporated and the residue crystallized from diethyl ether, to yield the 1-(3-acetylthiopropanoyl)-3,3-dimethylindoline-2-carboxamide melting at 156°–158°.

The solution of 0.04 g thereof in 5 ml of methanol and 5 ml of water is treated with 0.19 ml of 1N aqueous sodium hydroxide and the mixture stirred at room temperature under nitrogen for 1 hour. It is acidified with 0.5 ml of 6N hydrochloric acid, diluted with 5 ml of water and extracted with methylene chloride. The extract is dried and evaporated, to yield the 1-(3-mercaptopropanoyl)-3,3-dimethylindoline-2-carboxamide, melting at 232°–234°.

The starting material is prepared as follows:

The solution of 1 g of ethyl 3,3-dimethylindoline-2-carboxylate hydrochloride in 25 ml of ethanol is saturated with anhydrous ammonia and heated in a closed vessel to 50° for 4 days. It is evaporated, the residue crystallized from diethyl ether, suspended in water and 3N aqueous sodium hydroxide is added to render the mixture basic. It is extracted with methylene chloride, the extract dried and evaporated, to yield the 3,3-dimethylindoline-2-carboxamide melting at 156°–158°.

EXAMPLE 22

To the suspension of 1.0 g of 3,3-dimethylindoline-2-carboxylic acid hydrochloride in 25 ml of methylene chloride, 1.33 g of triethylamine are added and the resulting solution cooled to −10°. The solution of 1.065 g of 3-benzoylthio-2-methylpropanoyl chloride in 5 ml of methylene chloride is added dropwise and the mixture stirred at −5° for 1 hour, and then at room temperature for 2 hours. It is evaporated, 10 ml of 3N hydrochloric acid are added to the residue and the mixture is extracted with methylene chloride. The extract is dried and evaporated, to give the 1-(3-benzoylthio-2-methylpropanoyl)-3,3-dimethylindoline-2-carboxylic acid.

The solution of 1.2 g thereof in 40 ml of ethanol is saturated with gaseous ammonia at −5° to 0° for 1 hour, and at room temperature for 3 hours. The mixture is evaporated, the residue dissolved in 30 ml of water and 9 ml of saturated aqueous sodium bicarbonate, the solution is washed thrice with 25 ml of ethyl acetate and acidified with 5 ml of 6N hydrochloric acid. It is extracted with methylene chloride, the extract evaporated and the residue treated with 0.358 g of dicyclohexylamine in 5 ml of diethyl ether, to yield the dicyclohexylammonium 1-(3-mercapto-2-methylpropanoyl)-3,3-dimethylindoline-2-carboxylate melting at 212°–214°.

EXAMPLE 23

To the mixture of 0.65 g of 5,6-methylenedioxyindoline-2-carboxylic acid ethyl ester, 0.76 g of powdered potassium carbonate and 8 ml of methylene chloride is added 0.50 g of 3-acetylthio-2-methylpropanoyl chloride while stirring at room temperature. It is refluxed for 2 hours, poured into 16 ml of diethyl ether and washed with 8 ml of water, 8 ml of N hydrochloride acid and 8 ml of saturated aqueous sodium bicarbonate. The organic phase is separated, dried and evaporated. The residue is taken up in 5 ml of methanol and 4.0 ml of 2.03N aqueous potassium hydroxide are each deoxygenated by bubbling nitrogen through the solutions for 10 minutes. The latter solution is added to the former and the mixture stirred at room temperature under nitrogen. After 2 hours, 15 ml of 2N hydrochloric acid are added and the mixture is extracted thrice with 25 ml of diethyl ether. The extract is dried, evaporated, the residue taken up in 10 ml of diethyl ether and the solution combined with 0.44 g of dicyclohexylamine, producing a white precipitate. It is collected, washed thrice with 3 ml of diethyl ether and dried to give the dicyclohexylammonium 1-(3-mercapto-2-methylpropanoyl)-5,6-methylenedioxyindoline-2-carboxylate melting at 194°–196°.

The starting material is prepared as follows: 14.6 g of potassium are added slowly to 94 ml of ethanol in 1,125 ml of diethyl ether, followed by 54.8 g of diethyl oxalate and 68 g of 4,5-methylenedioxy-2-nitrotoluene. The mixture is stirred overnight at room temperature, the purple solid collected and washed thrice with 200 ml of diethyl ether, to give the potassium salt of 4,5-methylenedioxy-2-nitrophenylpyruvic acid ethyl ester, melting at 200°–202°. It is dissolved in 400 ml of acetic acid and the solution hydrogenated at 3 atmospheres over 0.8 g of platinum oxide for 2 hours. The suspension is filtered, the filtrate diluted with 1,200 ml of water and extracted 8 times with 200 ml of diethyl ether. The extract is dried and evaporated, to give the 5,6-methylenedioxyindole-2-carboxylic acid ethyl ester.

The mixture of 23 g thereof and 230 ml of 3N aqueous sodium hydroxide is refluxed for 30 minutes, cooled to room temperature, washed thrice with 150 ml of diethyl ether, and acidified to pH=1 with 60 ml of concentrated hydrochloric acid. The precipitate is collected, washed thrice with 25 ml of water and dried to give the corresponding acid melting at 243°–245°.

To the mixture of 15.5 g thereof, 18.9 g of triethylamine, 0.36 g of 4-dimethylaminopyridine and 45 ml of toluene, is added 16.1 g of acetic anhydride and the whole is stirred at room temperature overnight. Thereupon 75 ml of water and 75 ml of diethyl ether are added and the mixture is stirred for 2 hours. It is filtered, the filtrate diluted with 50 ml of diethyl ether and extracted thrice and 50 ml of water. The combined aqueous solutions are acidified to pH=1 with 15 ml of concentrated hydrochloric acid and the product collected, to give the 1-acetyl-5,6-methylenedioxyindole-2-carboxylic acid melting at 164°–166°.

The solution of 9.0 g thereof in 250 ml of ethanol is hydrogenated at atmospheric pressure over 0.36 g of platinum oxide for 48 hours. The suspension is filtered and the filtrate evaporated, to give the 1-acetyl-5,6-methylenedioxyindoline-2-carboxylic acid melting at 196°–200°.

Through the suspension of 7.5 g thereof in 375 ml of N hydrochloric acid nitrogen is bubbled for 5 minutes and then it is refluxed for 1.5 hours under nitrogen. It is cooled to room temperature, filtered and the filtrate evaporated, to give the 5,6-methylenedioxyindoline-2-carboxylic acid melting at 217°–220°.

Through the suspension of 1.0 g thereof in 10 ml of ethanol hydrogen chloride is bubbled for 30 minutes. It is stirred at room temperature for 2.5 hours, and evaporated. The residue is dissolved in 25 ml of saturated aqueous sodium bicarbonate, the solution extracted thrice with 20 ml of diethyl ether, the extract dried and evaporated, to give the corresponding ethyl ester as an oil.

EXAMPLE 24

To the stirred solution of 1.8 g of 5-hydroxyindoline-2-carboxylic acid ethyl ester in 50 ml of methylene chloride, is added 1.5 g of solid sodium bicarbonate, followed by 1.6 g of 3-acetylthio-2-methylpropanoyl chloride during 1 minute. The mixture is stirred for 3 hours at room temperature, diluted with 100 ml of methylene chloride and washed with 50 ml of water, 50 ml of 1N hydrochloric acid and 50 ml of saturated aqueous sodium bicarbonate. The organic layer is dried, evaporated and the residue taken up in 20 ml of methanol. This solution, and 17 ml of 2.03N aqueous potassium hydroxide, are each deoxygenated by bubbling nitrogen through for 10 minutes. The latter solution is added to the former and the mixture stirred for 2 hours at room temperature. It is combined with 50 ml of 1N hydrochloric acid, extracted thrice with 50 ml of methylene chloride, the extract dried and evaporated at room temperature. The residue is converted to its dicyclohexylamine salt as described previously, to yield the dicyclohexylammonium 1-(3-mercapto-2-methylpropanoyl)-5-hydroxyindoline-2-carboxylate melting at 208°–211°.

The starting material is prepared as follows: To the mixture of 10 g of 5-hydroxyindole-2-carboxylic acid, 29 g of triethylamine, 0.5 g of 4-dimethylaminopyridine and 50 ml of toluene, 23 g of acetic anhydride are added while stirring at room temperature. After 3 hours 150 ml of water are added and the mixture is stirred vigorously for 1 hour. The layers are separated, the organic phase is extracted with 50 ml of saturated aqueous sodium bicarbonate and the combined aqueous solutions washed with 100 ml of diethyl ether. They are acidified to pH=1 with concentrated hydrochloric acid, the precipitate formed is collected, washed 5 times with 50 ml of water and dried, to give the 1-acetyl-5-acetoxyindole-2-carboxylic acid melting at 142°–145°.

The solution of 10 g thereof in 100 ml of ethanol is hydrogenated at atmospheric pressure over 0.5 g of platinum oxide for 2.5 hours at room temperature. The suspension is filtered and the filtrate evaporated, to give the oily 1-acetyl-5-acetoxyindoline-2-carboxylic acid.

Through the suspension of 4.0 g thereof in 80 ml of 2N aqueous hydrochloric acid, nitrogen is bubbled for 5 minutes and the mixture refluxed under nitrogen for 2 hours. It is cooled to room temperature, filtered, the filtrate evaporated and the residue slurried in 25 ml of diethyl ether, to give the 5-hydroxyindoline-2-carboxylic acid hydrochloride melting at 238°–239°.

The solution of 3.2 g thereof in 30 ml of ethanol is saturated with gaseous hydrogen chloride and stirred at room temperature for 2 hours. It is concentrated under reduced pressure to 15 ml, 50 ml of diethyl ether are added and the resulting precipitate collected, to yield the corresponding ethyl ester melting at 206°–207°.

EXAMPLE 25

To the mixture of 1.583.5 g of indoline-2S-carboxylic acid ethyl ester, 21,000 ml of methylene chloride, and 3,859 g of powdered potassium carbonate, 1,690.2 g of 3-benzoylthio-2S-methylpropanoyl chloride in 5,000 ml of methylene chloride are added during 30 minutes while stirring at room temperature. The mixture is stirred for 2.5 hours at 40° and at room temperature overnight. It is filtered, the filtrate cooled to 17° and 673 g of hydrazine are added during 20 minutes. The mixture is stirred for 5 hours at room temperature, cooled to 17° and 10,000 ml of ice water and 5,000 ml of 4N hydrochloric acid are added while stirring. After about 30 minutes the organic layer is separated, washed twice each with 10,000 ml of 2N hydrochloric acid and 6,000 ml of saturated aqueous sodium chloride. It is dried, filtered and evaporated, to yield 1,907 g of 1-(3-mercapto-2S-methylpropanoyl)-indoline-2S-carboxylic acid ethyl ester.

To the solution of 1,897 g thereof in 14,850 ml of methanol, that of 345.5 g of lithium hydroxide in 5,900 ml of water is added during 30 minutes while stirring at room temperature. After 3.5 hours the mixture is cooled to 12°, diluted with 30,000 ml of water and combined with 4,000 ml of 4N hydrochloric acid at 10°–15°. The resulting suspension is stirred at 10° for 2 hours, filtered and the residue washed 4 times with 2,000 ml of water. 1,745 g thereof are taken up in 30,000 ml of diethyl ether, 174.6 g of charcoal are added and the mixture stirred for 15 minutes. It is filtered, the filtrate dried with 900 g of anhydrous sodium sulfate, filtered again and evaporated. 1,549 g of the residue are dissolved in 15,000 ml of toluene at 80° under nitrogen, the solution filtrate hot and stirred overnight at room temperature. The crystals formed are collected, washed twice with cold toluene and dried, to yield the 1-(3-mercapto-2S-methylpropanoyl)-indoline-2-carboxylic acid melting at 139°–141°, $[\alpha]_D^{23} = -170.4°$ (c=0.909 in ethanol); it is identical with that of Example 6.

EXAMPLE 26

Analogous to the methods illustrated by the previous examples, advantageously Examples 1–8 and 23–25, the following compounds of Formula II are prepared from equivalent amounts of the corresponding starting materials:

| No. | R | $C_mH_{2m}$ | Derivative | m.p. °C. or IR-bands cm$^{-1}$ |
|---|---|---|---|---|
| 1 | H | $(CH_2)_2$ | 2S—acid | 158–159 |
| 2 | H | $(CH_2)_2$ | 2S—ethyl ester and S—acetyl | 68–71 |
| 3 | 5-CH$_3$ | CH$_3$—CH—CH$_2$ | Ethyl ester and S—acetyl | 1720,1655, 1630 |
| 4 | 5-CH$_3$ | CH$_3$—CH—CH$_2$ | $(C_6H_{11})_2$NH—salt | 179–181 |
| 5 | 5-Cl | CH$_3$—CH—CH$_2$ | $(C_6H_{11})_2$NH—salt | 198–203 |
| 6 | 5-Cl | CH$_3$—CH—CH$_2$ | Ethyl ester and S—acetyl | 1710,1650, 1635 |

EXAMPLE 27

Preparation of 10,000 tablets each containing 5 mg of the active ingredient of Example 6:

| Formula: | |
|---|---|
| 1-(3-mercapto-2S—methylpropanoyl)-indoline-2S—carboxylic acid | 50.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 28

Preparation of 10,000 capsules each containing 10 mg of the active ingredient of Example 6:

| Formula: | |
|---|---|
| 1-(3-mercapto-2S—methylpropanoyl)-indoline-2S—carboxylic acid | 100.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Analogously tablets or capsules are prepared from the remaining compounds of the invention, e.g., those illustrated by the other examples herein.

We claim:

1. A 1-mercaptoalkanoylindoline-2-carboxylic acid compound of the formula:

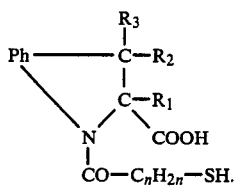

wherein Ph is unsubstituted 1,2-phenylene, or 1,2-phenylene substituted by one or two members selected from lower alkyl, lower alkoxy, hydroxy, and halogeno, or 1,2-phenylene substituted by one member selected from lower alkylenedioxy and trifluoromethyl; each of $R_1$, $R_2$ and $R_3$ is hydrogen or lower alkyl; and n is an integer from 1 to 7; the S-lower alkanolyl or the S-HPh-carbonyl derivative thereof; the amide, the lower alkyl ester; or a pharmaceutically acceptable salt of said carboxylic acid.

2. A compound as claimed in claim 1, wherein Ph is 1,2-phenylene, unsubstituted or substituted by methyl, methoxy, methylenedioxy, hydroxy, chloro or trifluoromethyl; and each of $R_1$, $R_2$ and $R_3$ is hydrogen or methyl.

3. A compound as claimed in claim 1 and corresponding to the formula

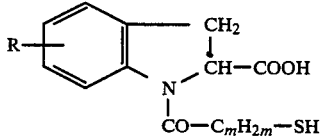

wherein R is hydrogen, alkyl or alkoxy with up to 4 carbon atoms, halogeno or trifluoromethyl; and m is an integer from 2 to 4; the S-lower alkanoyl or benzoyl derivatives thereof; lower alkyl esters or pharmaceutically acceptable alkali metal or ammonium salts of said acids.

4. A compound as claimed in claim 3, in which formula R is hydrogen, methyl, methoxy, fluoro, chloro or trifluoromethyl, and $C_mH_{2m}$ is ethylene or 1,2-propylene.

5. A compound as claimed in claim 3, wherein R is in the 5-indoline-position.

6. A compound as claimed in claim 4, in the form of its levorotatory optical antipode thereof, with a 2S-carboxy and 2S-methyl within said indoline and 1,2-propylene moieties respectively.

7. A compound as claimed in claim 6, being the 1-(3-mercapto-2S-methylpropanoyl)-indoline-2S-carboxylic acid; or a pharmaceutically acceptable alkali metal or ammonium salt thereof.

8. A compound as claimed in claim 6, being the 1-(3-mercaptopropanoyl)-indoline-2S-carboxylic acid; or a pharmaceutically accetptable alkali metal or ammonium salt thereof.

9. An antihypertensive and cardioactive pharmaceutical composition comprising a correspondingly effective amount of a compound as claimed in claim 1, together with a pharmaceutical excipient.

10. A method of treating hypertension or congestive heart failure in mammals, which consists in administering to said mammals in need thereof, an effective amount of a composition claimed in claim 9.

11. A compound of the formula

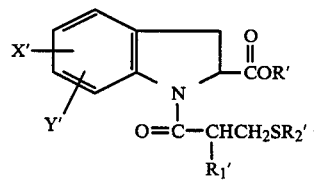

wherein
$R_1'$ is H or $CH_3$,
$R'$ is H or lower alkyl,
$X'$ is H, methoxy, hydroxy, Cl or $CH_3$,
$Y'$ is H or methoxy,
$R_2'$ is H, lower alkanoyl or benzoyl,
or $X'$ and $Y'$ are on adjacent carbon atoms and together form a methylenedioxy group.

* * * * *